(12) United States Patent
Gurman (10) Patent No.: US 9,597,424 B2
(45) Date of Patent: Mar. 21, 2017

(54) FIBERGLASS DIELECTRIC BARRIER IONIZATION DISCHARGE DEVICE

(71) Applicant: Clean Air Group, Inc., Fairfield, CT (US)

(72) Inventor: Hal Ross Gurman, Scottsdale, AZ (US)

(73) Assignee: Clean Air Group, Inc., Fairfield, CT (US)

( * ) Notice: Subject to any disclaimer, the term of this patent is extended or adjusted under 35 U.S.C. 154(b) by 0 days.

(21) Appl. No.: 14/799,768

(22) Filed: Jul. 15, 2015

(65) Prior Publication Data

US 2015/0314033 A1  Nov. 5, 2015

Related U.S. Application Data

(62) Division of application No. 13/623,209, filed on Sep. 20, 2012, now Pat. No. 9,114,356.

(51) Int. Cl.
| | | |
|---|---|---|
| *A61L 9/22* | (2006.01) | |
| *B01D 53/32* | (2006.01) | |
| *B03C 3/38* | (2006.01) | |
| *B03C 3/41* | (2006.01) | |
| *F24F 3/16* | (2006.01) | |

(52) U.S. Cl.
CPC ............... *A61L 9/22* (2013.01); *B01D 53/32* (2013.01); *B03C 3/38* (2013.01); *B03C 3/41* (2013.01); *B01D 2257/90* (2013.01); *B01D 2258/06* (2013.01); *B01D 2259/4508* (2013.01); *B01D 2259/818* (2013.01); *F24F 3/166* (2013.01); *Y10T 29/49002* (2015.01); *Y10T 29/49144* (2015.01); *Y10T 29/49149* (2015.01)

(58) Field of Classification Search
CPC .. A61L 9/22; B01D 53/32; B03C 3/41; B03C 3/38
See application file for complete search history.

(56) References Cited

U.S. PATENT DOCUMENTS

| | | | | |
|---|---|---|---|---|
| 6,018,502 A | * | 1/2000 | Fry, Jr. ................... | G01V 1/157 367/147 |
| 7,312,973 B2 | * | 12/2007 | Sekoguchi ............... | A61L 9/22 361/231 |
| 2006/0002051 A1 | * | 1/2006 | Goudy, Jr. .............. | C01B 13/11 361/220 |
| 2010/0247389 A1 | * | 9/2010 | Abate ...................... | B03C 3/49 422/121 |
| 2012/0154973 A1 | * | 6/2012 | Vaynerman ............. | B03C 3/383 361/231 |

(Continued)

FOREIGN PATENT DOCUMENTS

WO       9920388 A2    4/1999

*Primary Examiner* — Regina M Yoo
(74) *Attorney, Agent, or Firm* — Abelman, Frayne & Schwab (57) ABSTRACT

A bipolar ionization device in which fiberglass is used as the dielectric. In one embodiment, a fiberglass board is used, with the anode on one side of the board and the cathode on the other side of the board. A number of flat boards can be stacked, with spacing between them to allow air flow to scavenge ions, with stanchions providing both mounting and electrical connections to the ionization devices. In another embodiment, a fiberglass tube is used, with the cathode inside the tube and the anode outside the tube.

5 Claims, 11 Drawing Sheets

(56) References Cited

U.S. PATENT DOCUMENTS

2012/0287551 A1* 11/2012 Waddell ................ B03C 3/383
 361/230
2013/0285777 A1* 10/2013 Piascik .................... H01F 5/04
 335/299

* cited by examiner

FIBERGLASS DIELECTRIC BARRIER IONIZATION DISCHARGE DEVICE

RELATED APPLICATION

This application claims priority to and is a divisional of U.S. patent application Ser. No. 13/623,209 filed on 20 Sep. 2012. The entirety of the cited disclosure is hereby incorporated by reference.

BACKGROUND OF THE INVENTION

1. Field of the Invention

The present invention relates generally to air purifiers, and more specifically to bipolar ionization devices for use in heating, ventilation and cooling (HVAC) systems to reduce the number of air particulates and break down chemical compounds that cause odors.

2. Description of the Related Art

Indoor air environments frequently include suspended particulates, such as dust, dander, soot and smoke particles, pollen, mold, bacteria, and viruses. Indoor gases are also present, being released from building materials, home furnishings and nondurable goods. In office environments, the greater user of machines, such as photocopying equipment and the like, is especially problematic, as this equipment may emit volatile organic compounds.

These particulates can degrade the quality of the air, making it less pleasant and even dangerous to occupants of the space. Modern construction techniques that promote energy efficiency, such as insulating walls, ceilings, doors and windows, and wrapping buildings with air intrusion barriers, have created spaces that are so airtight that the buildings are unable to release the off-gas toxic elements.

In ordinary heating, ventilation and cooling (HVAC) systems, air is drawn through a filter, which is intended to trap particulates in the filter. However, traditional filters are only effective for large particles of at least 10 microns in size. While high efficiency particle air (HEPA) filters are more effective, they also have disadvantages, as they may quickly become clogged, requiring frequent changing to avoid overburdening the HVAC equipment. Because of the presence of contaminants in the air and the general inability of physical filters to remove the same, a condition known as "sick building syndrome" has developed. Various building codes designed to mitigate this syndrome have been introduced; for example, the American Society of Heating, Refrigeration & Air Conditioning Engineers (ASHRAE) recommends a minimum of 8.4 air exchanges in a 24-hour period (a 35% turnover rate). While commercial and industrial facilities generally meet that minimum level, their air quality may remain inferior. Furthermore, there are many houses that do not even meet such minimum levels. While greater turnover rates would increase the interior air quality, they would also reduce the buildings' energy efficiencies.

An alternative method to filtering involves the use of ionization generated from non-thermal plasma technology to remove contaminants from air. Ionization occurs where an atom or group of atoms loses or gains one or more electrons. An electrically neutral atom or molecule will have an equal number of electrons and protons. If an electron bound to an atom or molecule absorbs enough energy from an external source, it may exceed the ionization potential and allow the electron to escape its atomic orbital. When this occurs, the electron is lost, and an ion with a positive electrical charge, a cation, is produced. Electrons that are lost become free electrons. When a free electron later collides with an atom, it may be captured within an orbital. The gain of an electron by an atom or molecule creates an ion with a negative electrical charge, an anion.

The ionization of air, e.g., air in the Earth's atmosphere, results in the ionization of the air's constituent molecules, primarily oxygen and nitrogen. While the nitrogen in air is more plentiful than oxygen, oxygen is more reactive. Thus, oxygen has a lower ionization potential than nitrogen, allowing for oxygen cations to be formed with greater ease than nitrogen cations, and oxygen has a higher electro-negativity than nitrogen, allowing for oxygen anions to be formed with greater ease than nitrogen anions.

Ionization is known to break down organic chemicals into the basic molecular constituents of water, carbon dioxide, and related metal oxides. Thus, ionization has potential for cleaning indoor air, by eliminating chemical pollutants and their associated odors from the enclosed environment. Ionization also contributes to the reduction of particulate matter, by imparting a charge to those particles: the charge causes the smaller particles to agglomerate, or clump together, forming larger particles that then drop out of the air or become caught in a filter system.

Studies indicate that an overbalance of positive to negative ions (cations) may impair human health in a number of ways, such as by stimulating increased production of the neurohormone serotonin, which may lead to exhaustion, anxiety and depression. Positive ions are frequently found in offices where VDUs (visual display units) are used. Negative ions (anions) have a calming effect. Thus, a machine that cleans indoor air should seek to introduce negative ions into the airstream.

Various commercial products have been made including machines that incorporate bipolar ionization devices. The ionization of air may also produce ozone, $O_3$, whose levels should be kept below standard limits. Therefore, there is demand for a system which provides a sufficient level of ionization to effectively address the contaminants in an airstream, and in which the levels of ozone can be controlled.

Under the circumstances, it would be highly desirable to use ionization technology for air treatment, and indeed there are many suppliers of bipolar ionization devices that are stand-alone devices used in specified locations, or centralized installations which are integrated into a building HVAC system. These devices are used in a way so that air circulated into and recirculated within the building can pass over the bipolar emitting devices. This can accomplish the goal of improving air quality, without mandating greater air exchange rates. Thus, an additional benefit of ionization treatment of indoor air is that it contributes to the efficiency of HVAC operations.

Commercially available bipolar ionization devices generally apply glass tubes as dielectrics. However, glass tubes are relatively fragile, encountering numerous mechanical failures during shipping, due to mishandling, and due to stress-related failures at higher ambient temperatures. In addition, the shape and arrangement of the glass tubes can in some instances impede the air flow, thus harming efficiency. Therefore, there is a need in the art for an improved, efficient bipolar ionization device with low manufacturing costs and a reduced mechanical failure rate. In addition, there is a need in the art for a bipolar ionization device with an aerodynamic shape that provides for more efficient air flow, allowing greater scavenging of ions and simplifying installation in a wider range of HVAC systems or stand-alone devices.

BRIEF SUMMARY OF THE INVENTION

The present invention discloses a bipolar ionization device for use with heating, ventilation and cooling (HVAC) systems and stand-alone devices, and providing low manufacturing costs, a reduced mechanical failure rate, and high efficiency.

In one embodiment, the bipolar ionization device includes a flat fiberglass-reinforced epoxy laminate board that serves as the dielectric. A thin layer of solid copper foil is laminated to one side of the board, forming a copper-clad laminate that serves as a cathode of the bipolar ionization device. The second side of the board is provided with an anode fabricated from a tightly woven metallic mesh or grid. The fiberglass board is much more durable than ionization devices using a glass dielectric, and can be produced at a low cost and high efficiency. In addition, the flat design simplifies the placement of the devices in a broad range of locations, with improved ion scavenging that allows further efficiencies.

In a second embodiment, the bipolar ionization device is designed around a fiberglass-reinforced epoxy laminate tube. Provided inside the tube is a metal cathode, which can be solid metal, or a mesh or perforated metal. Outside the tube, a metallic mesh or grid anode is provided. While this embodiment would not offer the improved ion scavenging that the flat design can offer, it would still be advantageous in terms of its mechanical strength, high efficiency, and low manufacturing cost. In addition, the tubular design would allow a retrofit of existing ionization systems that currently employ glass tube ionization devices.

Both the flat fiberglass board design and the fiberglass tube design are adapted for mechanical and electrical connectivity to an AC power supply. In the second embodiment of the fiberglass tube, the conducting terminal includes a power input terminal extending from the bottom surface of the end cap for providing current to the cathode via a current distributor. A stainless steel clip or wire from a second terminal of the power supply can be coupled to the anode to complete the circuit.

In the first embodiment in which the ionization device is designed on a flat fiberglass board, a preferred embodiment provides for a number of the ionization devices to be mounted on a set of three stanchions affixed to a terminal box. With each board forming a roughly rectangular shape, one narrow end of the boards will be supported by a first and second stanchion, with the other narrow end of the boards being supported by the third stanchion. In a preferred embodiment, the boards are notched to accommodate the mounting via the three stanchions. In another preferred embodiment, in addition to providing structural support for mounting, the first and second stanchion provide high voltage alternating current for the ionization devices, with the currents referred to in this application as HV+ and HV−. In yet another preferred embodiment, the third stanchion is designed to allow for easy mounting and dismounting of each board.

BRIEF DESCRIPTION OF THE DRAWINGS

Further advantages and features of the present invention will become apparent from the detailed description of a preferred embodiment of the invention with reference to the accompanying drawings, in which.

To facilitate understanding of the invention, identical reference numerals have been used, when appropriate, to designate the same or similar elements that are common to the figures. Further, unless stated otherwise, the drawings shown and discussed in the figures are not drawn to scale, but are shown for illustrative purposes only.

DETAILED DESCRIPTION OF THE INVENTION

One embodiment of the present invention is a ionization device for removing impurities, such as dust, pollen, mold, compounds producing noxious odors, among other undesirable particles from the air, that manifest themselves, illustratively, in ventilation systems of buildings, although such environment is not considered as being limiting.

Among the improvements in the tube of the present invention is the improvement in overall structural integrity.

Both the flat fiberglass board ionization device and the fiberglass tube ionization device provide for an anode and cathode which increase the ion output of the ionization tube. The mesh or grid used to form the anode is fabricated with a tightly woven mesh, which allows for more contact points to produce ions.

In addition to other benefits, the embodiment of the flat fiberglass ionization device results in a reduction in the resistance to airflow, allowing for a more efficient HVAC system.

Reference will now be made in detail to implementations of the invention, examples of which are illustrated in the accompanying drawings.

Figure 1:
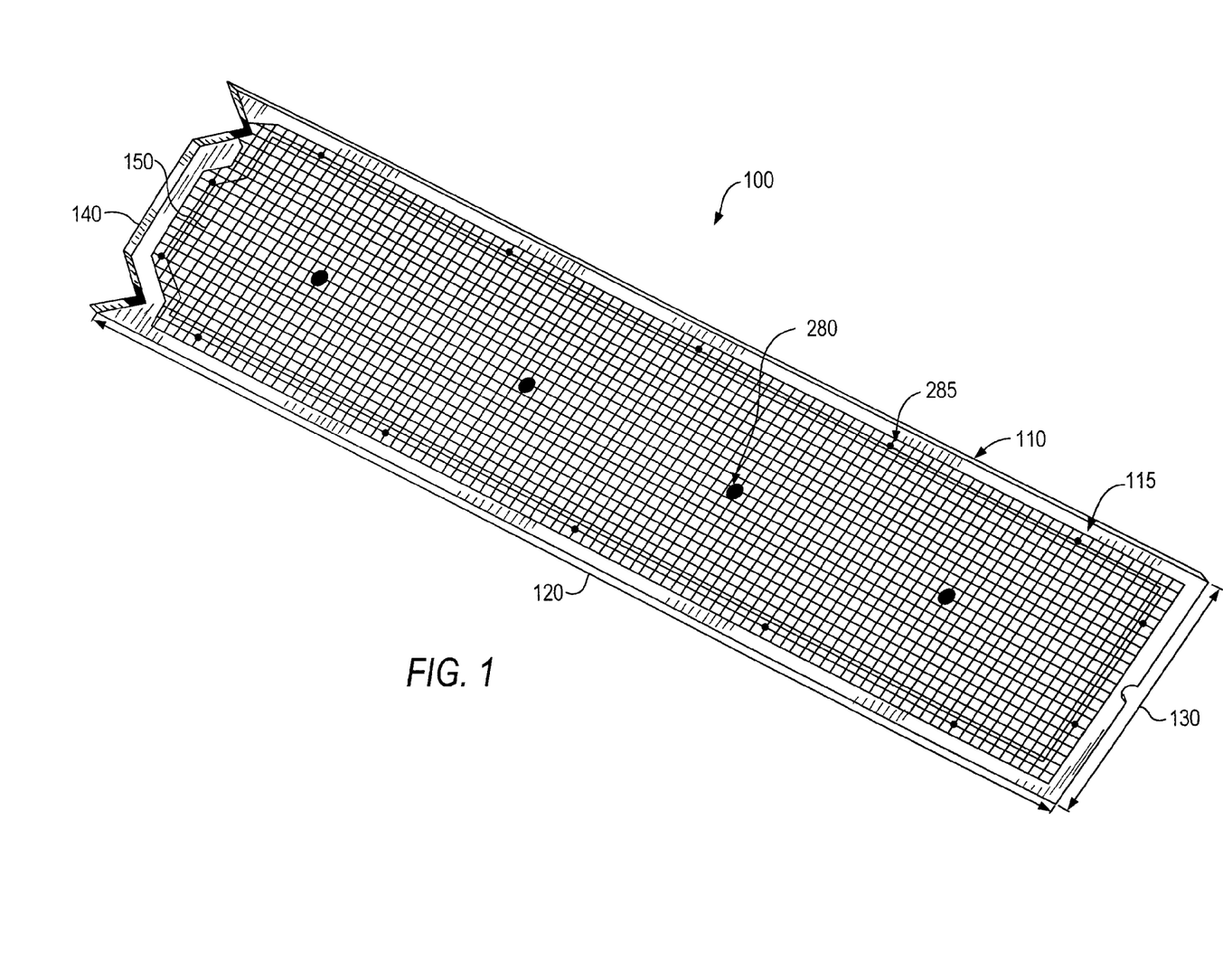
FIG. 1 is a perspective view of the anode of an embodiment of an ionization device designed on a flat fiberglass board, as assembled, in accordance with the present invention.
Figure 2:
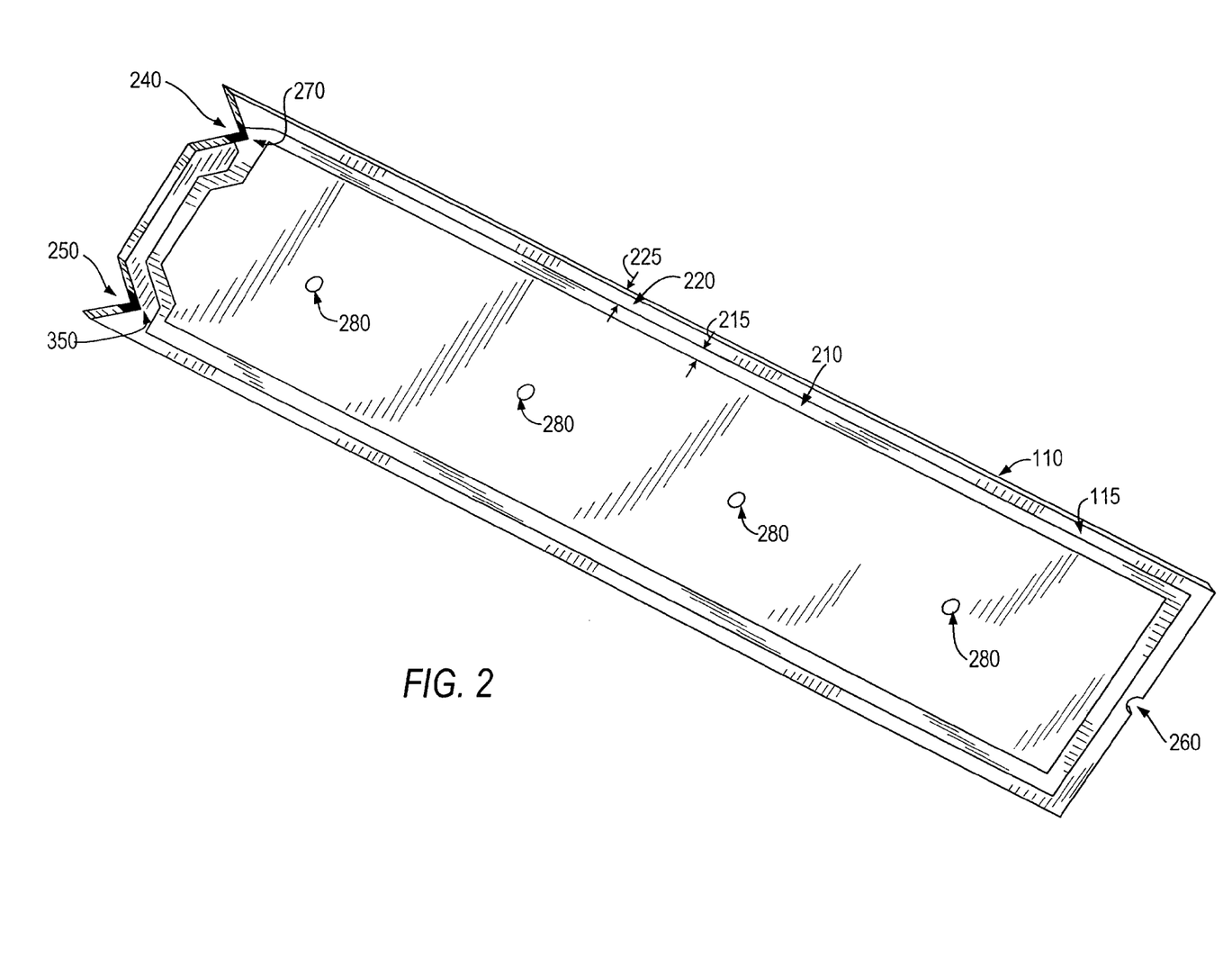
FIG. 2 is a perspective view of the anode of the ionization device, before the mesh or grid is installed.
Figure 3:
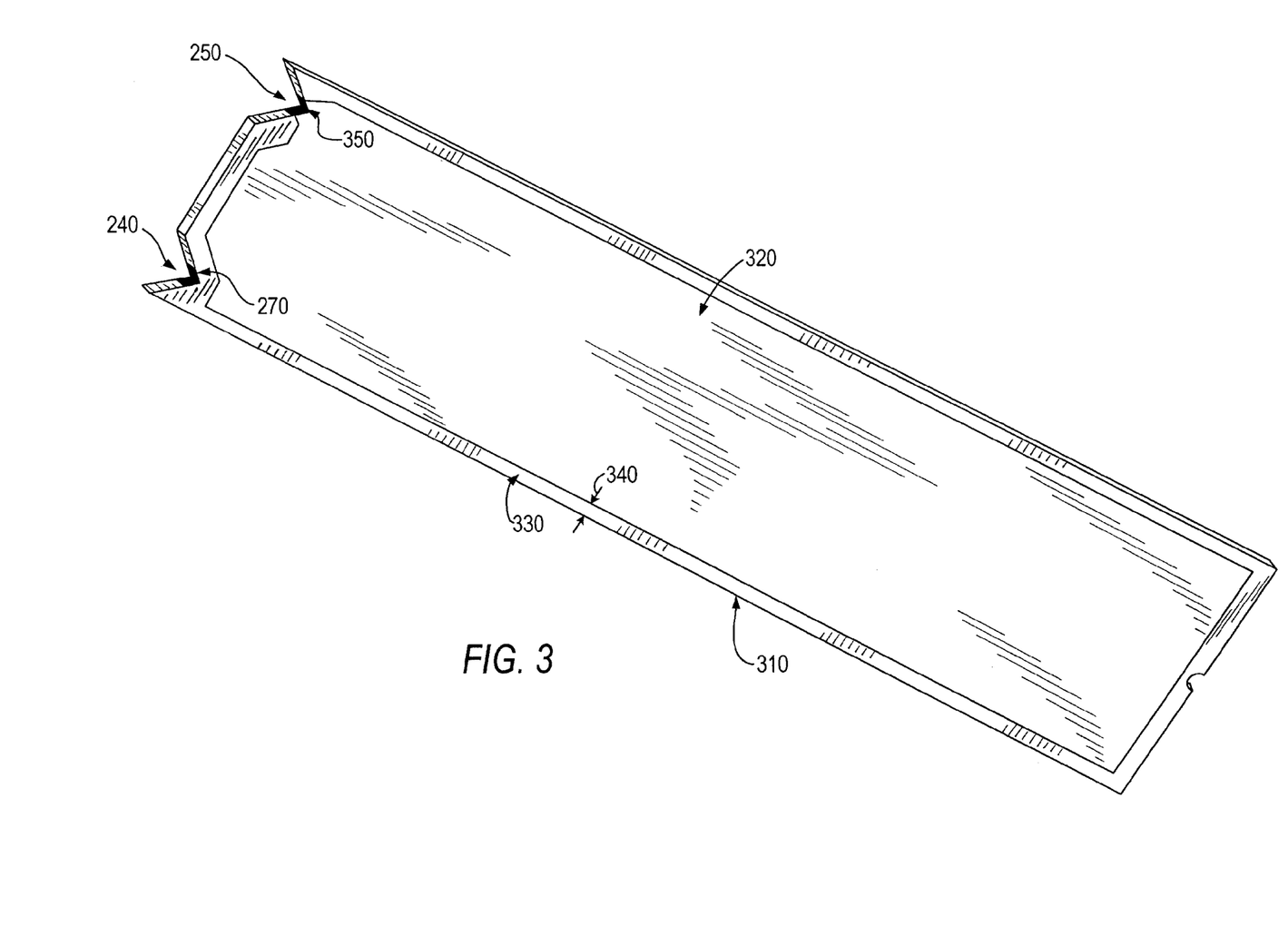
FIG. 3 is a perspective view of the cathode of the ionization device.

FIGS. 1-3 illustrate an embodiment of an ionization device 100 in which a flat fiberglass-reinforced epoxy laminate board 110 serves as the dielectric. The fiberglass-reinforced epoxy laminate board 110 is preferably rated a FR-4 grade, a popular laminate grade that provides a good strength-to-weight ratio, providing electrical insulation with considerable mechanical strength. However, other materials that provide structural integrity, durability, and efficient operational performance can be substituted.

As FIG. 1 illustrates, the board 110 has a length 120 and width 130 that far exceed the thickness 140. The board 110 thus has a top and bottom and four very short sides. The top, of length 120 and width 130, is designated as anode 115, and the bottom, also of length 120 and width 130, is designated as cathode 310. Ionization device 100 can be constructed on boards of a variety of shapes and sizes, including not only a rectangular shape, as shown, but also a square shape, a circular shape, elliptical shape, etc. The assignee of the rights to this invention intends to commercialize embodiments of ionization device 100 in a number of rectangular and circular shapes, and reserves the rights to other shapes. In a preferred rectangular embodiment, the length, width and thickness of board 110 is 17.5"×5.5"×0.125". However, this should not be considered limiting, as a wide variety of sizes and shapes are possible.

FIGS. 1 and 2 illustrate the anode side 115 of the board 110, with FIG. 1 representing the assembled anode and FIG. 2 representing an earlier stage of the anode before final assembly. FIG. 3 illustrates the cathode 310 of the board 110.

Figure 4:
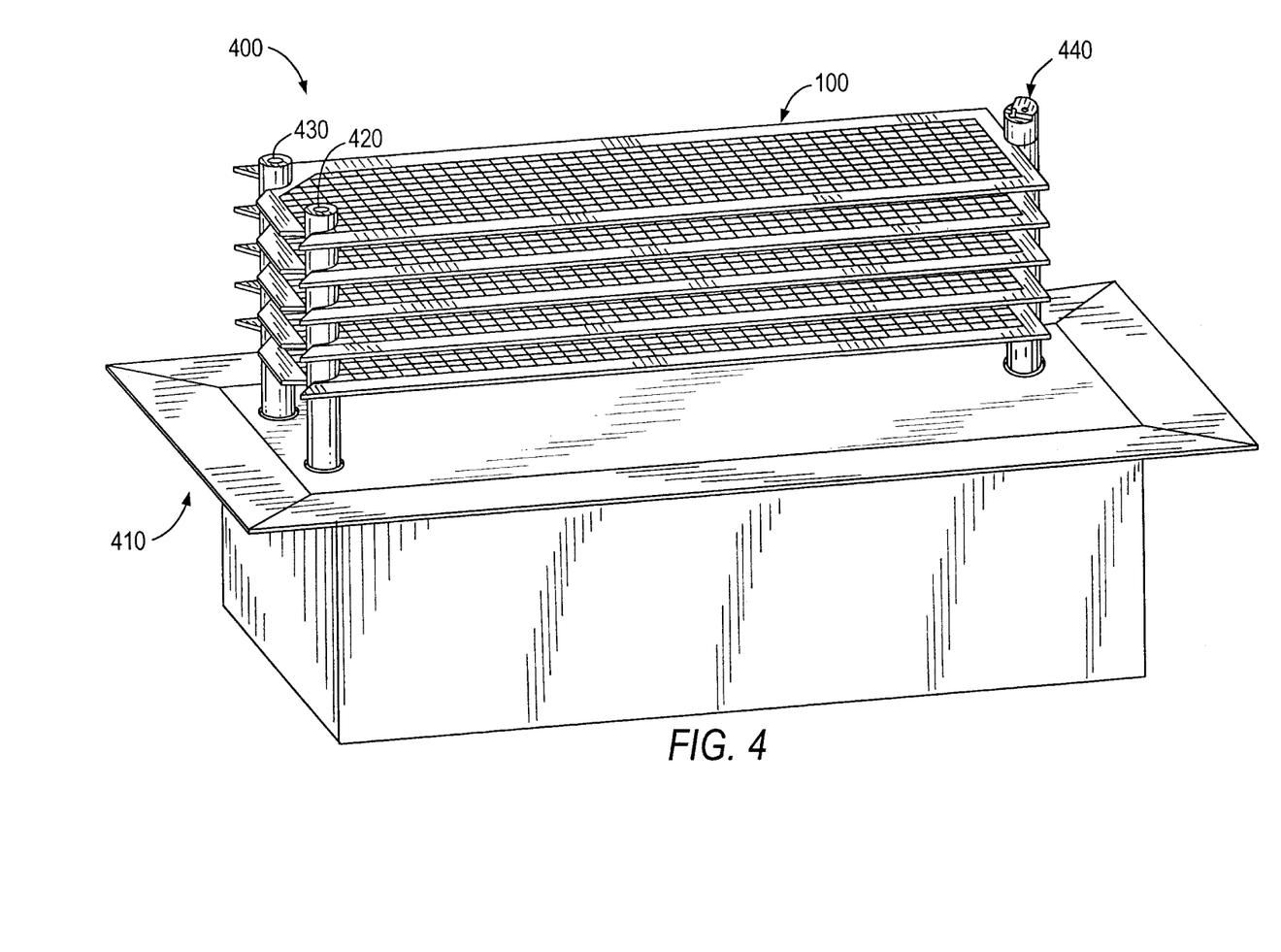
FIG. 4 is a perspective view of an ionization system incorporating a plurality of flat fiberglass board ionization devices.

In an embodiment such as shown in FIG. 4, one or more ionization devices 100 can be mounted on first stanchion 420, second stanchion 430, and third stanchion 440. To accommodate such an embodiment, and referring back to FIG. 2, board 110 includes concave notches 240 and 250 on one end of the board, and a single concave notch 260 on the other end of the board. First stanchion 420 is engaged by notch 250 of board 110, second stanchion 430 is engaged by notch 240 of board 110, and third stanchion 440 is engaged by notch 260 of board 110.

FIG. 3 presents a preferred embodiment in which cathode 310 is provided with a solid copper face 320 that covers most of the area of the bottom of board 110. A border 330 of width 340 that is free from the solid copper face 320 surrounds the perimeter of cathode 310. In a preferred embodiment, the solid copper face 320 has a thickness of approximately 1 ounce weight of copper per square foot, being approximately 1.34 mils or 34 micrometers, representing approximately 1 ounce of copper per square foot. In a preferred embodiment, width 340 is 0.5".

For corrosion resistance, solid copper face 320 is preferably provided with tinning. In an alternative embodiment, cathode 310 can be provided with a conductive material other than copper. In other alternative embodiments, cathode 310 can use a mesh or perforated metal in lieu of the solid face 320 shown.

With reference to FIG. 2, anode 115 of board 110 is provided with a tracing 210 of copper, preferably provided with tinning. Tracing 210 has width 215 and roughly follows the perimeter of the top of board 110, inside of a border 220 with width 225. In a preferred embodiment, the width 225 of border 220 is 0.5", and the width 215 of tracing 210 is 0.25". Anode 115 is also provided with a plurality of attachment dots 280 that are also copper, preferably provided with tinning. In a preferred embodiment, attachment dots 280 are 0.25" in diameter. In a preferred embodiment, the copper of tracing 210 and attachment dots 280 have a thickness of approximately 1 ounce weight of copper per square foot.

The board 110 can be purchased from a manufacturer with copper already applied to both sides, and the copper can then be removed from unwanted areas by various subtractive methods leaving only the desired copper traces. Alternatively, the board 110 can be produced using an additive method where traces are adding to the bare substrate by electroplating methods.

In one embodiment, screen 150, shown in FIG. 1, is tacked down to attachment dots 280, as well as being tacked down to tracing 210, as shown with small attachment dots 285. The number and spacing of attachment dots 280 and 285 as shown is not intended to be limiting. Screen 150 is preferably aluminum or stainless steel, and is die cut to match the exact size and shape of tracing 210. Screen 150 is provided with a plurality of interstitial spaces or perforations of approximately 180 to 290 openings per square inch. In one embodiment, the anode includes approximately 225 openings per square inch. With screen 150 tacked down and thus being in close contact to the dielectric, the ionization device yields a high ion output and a relatively low ozone production.

Ion and ozone outputs are affected by the thickness of the dielectric and the spacing of the screen 150 from the dielectric; by adjusting these two variables, ion and ozone outputs can be tailored to suit the application. Thus in another embodiment, not shown, conductive spacers are provided between tracing 210 and screen 150, and between attachment dots 280 and screen 150. In a preferred embodiment, the conductive spacers will add 7 mil spacing.

With reference to FIGS. 2 and 3, one preferred embodiment is that first stanchion 420 and second stanchion 430 not only provide structural support for board 110, but also provide for the supply of HV+ and HV− alternating current to the ionization device 100. Voltage for the anode 115 of the board 110 is supplied by the second stanchion 430, at the intersection 270 between notch 240 and the second stanchion 430. Voltage for the cathode 310 of the board 110 is supplied by the first stanchion 420, at the intersection 350 between notch 250 and the first stanchion 420.

Ionization device 100 is powered by a high voltage alternating current (ac). In a preferred embodiment, ionization devices 100 will be powered by 2000-3,000 volts ac, which can be supplied by a power transformer that raises a branch circuit from 120 or 220 volts ac up to 3,000 volts ac. Cathode 310 thus experiences one polarity from first stanchion 420 while anode 115 experiences the opposite polarity from second stanchion 430. This leads to opposite charges to build-up on each side of the dielectric barrier, with the resultant electric field generating discharges in the form of plasma filamentary and surface dielectric barrier discharges (DBD).

As air flows over the ionization device 100 and the molecules in the air interact with the generated plasma, electrons are transferred between molecules, generating both positive and negative ions that propagate quickly, thus ionizing the air. Ionization of the air helps clean the air by breaking down organic chemicals and removing their associated odors, as well as reducing the levels of particulate matter through agglomeration.

In this preferred embodiment, the first and second stanchions provide HV+ and HV− voltage to the side of the board 110 indicated by width 140. In a preferred embodiment, on cathode 310, border 330 is interrupted at the intersection 350 of notch 250 and first stanchion 420. Instead, solid copper face 320 extends to the edge of cathode 310 and over the edge, onto the side of the board 110 indicated by width 140, making contact with the HV+ terminal of the power supply through the conductor of first stanchion 420. Similarly, on the anode 115, border 220 is interrupted at the intersection 270 of notch 240 and second stanchion 430. Instead, trace 210 extends to the edge of anode 115 and over the edge, onto the side of the board 110 indicated by width 140, making contact with the HV− terminal of the power supply through the conductor of second stanchion 430.

FIG. 4 illustrates an ionization system 400 in which a plurality of ionization devices 100 are mounted horizontally, with the anode (top) surface facing up and the cathode (bottom) surface facing down. In a preferred embodiment, ionization devices 100 are spaced 0.7" from the top of a lower board to the bottom of an upper board. Ionization devices 100 are notched as discussed earlier, and fit into mounting and power stanchions 420, 430 and 440. The stanchions, in turn, are mounted to a baseplate on enclosure 410, in which enclosure 410 may incorporate a power transformer and monitoring electronics (not shown). Ionization system 400 could be placed, for example, in an HVAC duct, providing ionized particles into the airstream.

Figure 5:
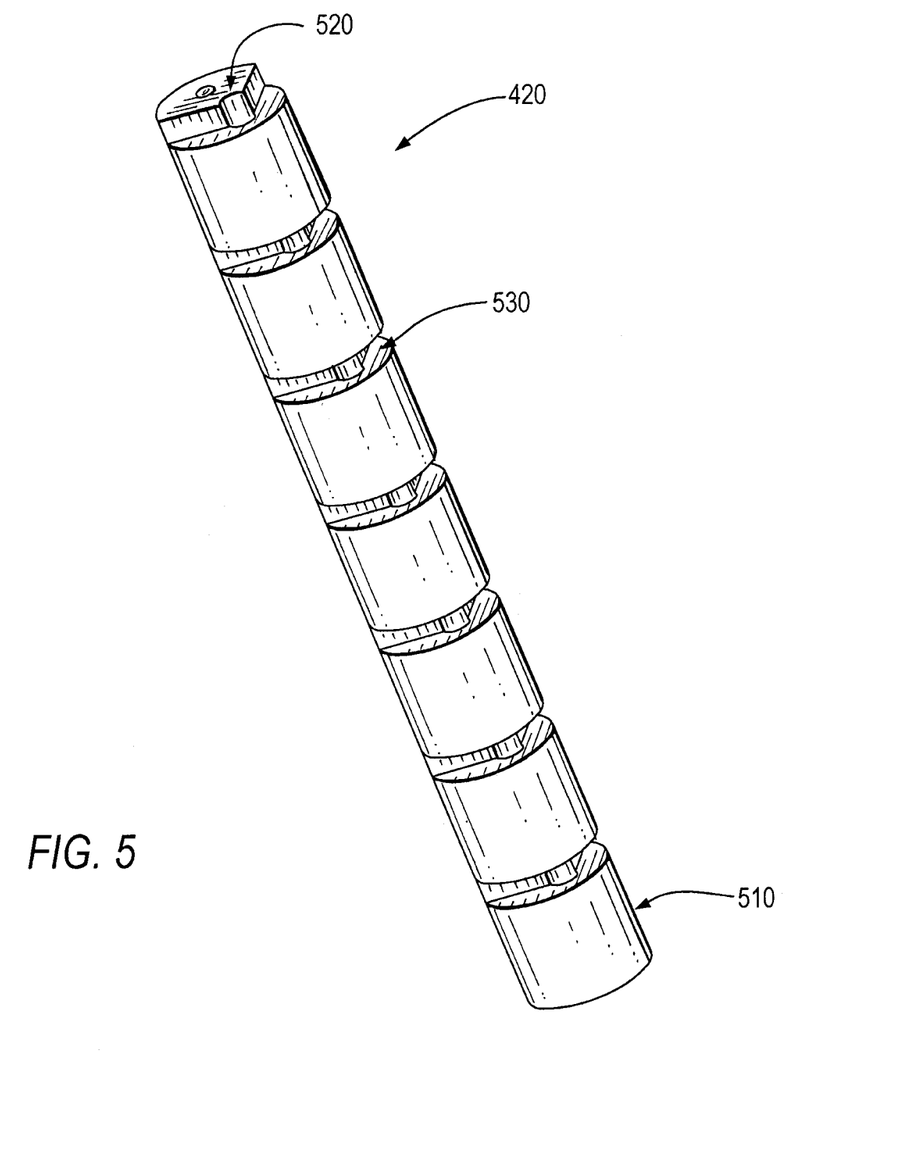
FIG. 5 is a perspective view of a support and power stanchion for mounting a fiberglass board ionization device.

FIG. 5 is a perspective detail of first stanchion 420, with first stanchion 430 being identical. Stanchions 420 and 430 comprise a plurality of modular insulators 510 surrounding a central conductor (not shown), which also provides structural support. Modular insulators 510 are provided with bore hole 520 to accommodate the central conductor. In a preferred embodiment, central conductor 520 is a #304 stainless steel threaded rod.

Figure 6:
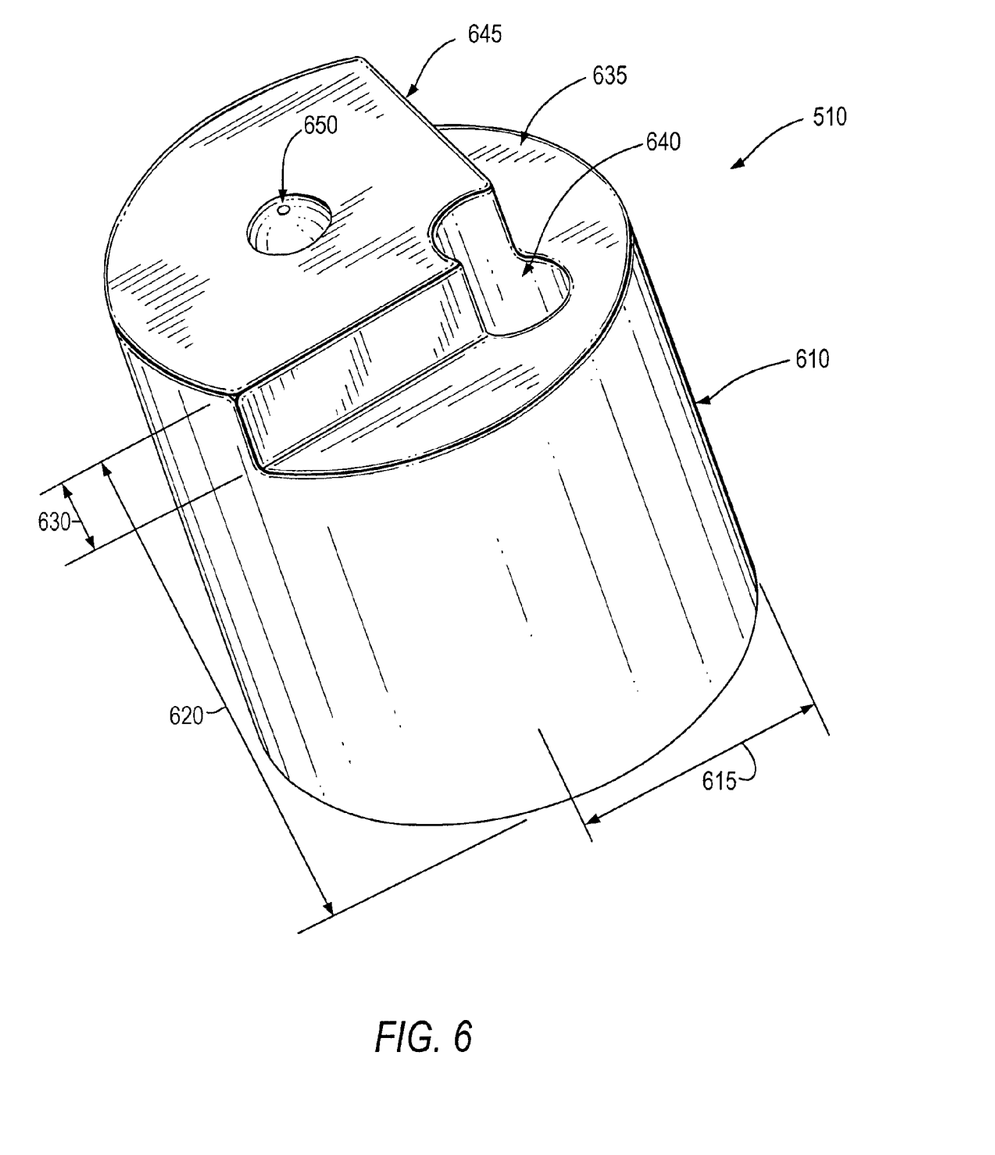
FIG. 6 is a perspective view of a modular insulator, two or more of which are assembled into a support and power stanchion for mounting a fiberglass board ionization device.

FIG. 6 is a detail of a single modular insulator 510. Each is roughly cylindrical, with radius 615 and height 620. At the top of modular insulator 510, a portion of the circumference is cut away to a depth 630, with depth 630 being slightly larger than the thickness 140 of board 110. The cut away circumference leaves a surface 635 above which is a convex v-shaped notch 645 that provides support for concave notches 240 and 250 of board 110. At the top of modular insulator 510 is a convex hemisphere 650, with the bottom of modular insulator 510 having a corresponding concave hemisphere (not shown). A bore hole 640 is supplied so that modular insulator 510 can be slipped over central conductor 520. A plurality of modular insulators 510 can thus be stacked one of top of the other, with central conductor 520 preventing lateral movement of the modular insulators 510, and the mating of the convex hemisphere 650 and concave hemisphere preventing rotational movement of the stacked modular insulators 510.

A stanchion has a minimum of two modular insulators 510, to retain a single board 110, but by varying the height of central conductor 520 and the number of modular insulators 510, a stanchion can be built to support any of a plurality of boards 110. The threaded rod that forms the central conductor and structural support is cut to the appropriate length, depending on the number of modular insulators 510. For five modular insulators, the rod would be approximately 80 mm long. It is envisioned that up to ten modular insulators can be accommodated. The Insulator 510 is Noryl plastic or equivalent. At the base of the stack of modular insulators, the threaded rod penetrates the baseplate on the enclosure. At the top of the stack of modular insulators, washers and nuts are used to retain top modular insulator 510 in place vertically.

Figure 7:
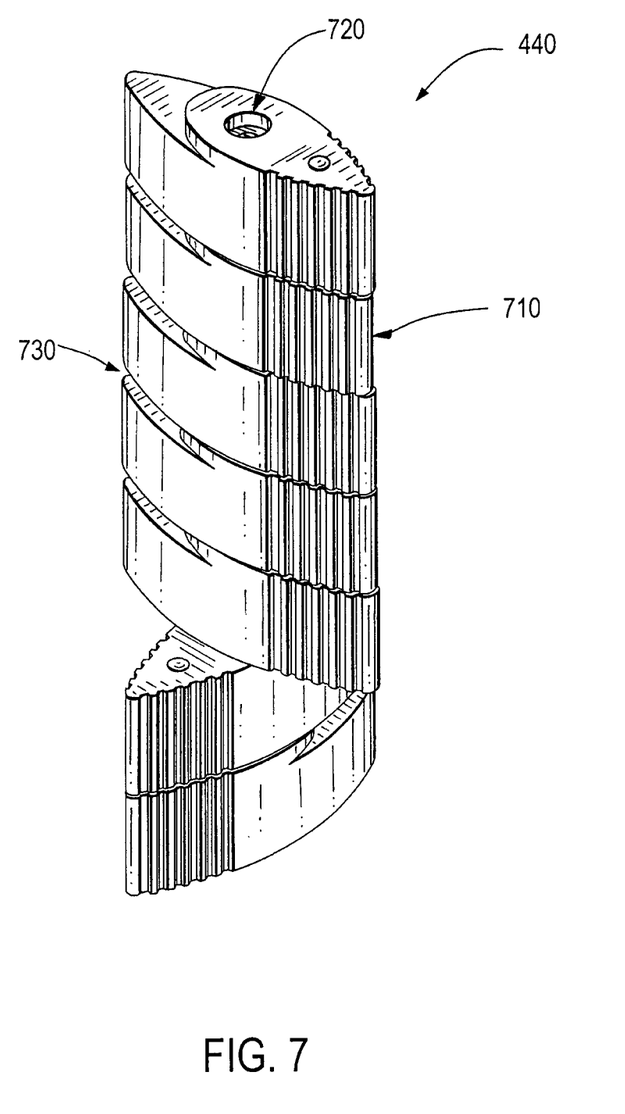
FIG. 7 is a perspective view of a quick-release support stanchion for mounting a fiberglass board ionization device.
Figure 8:
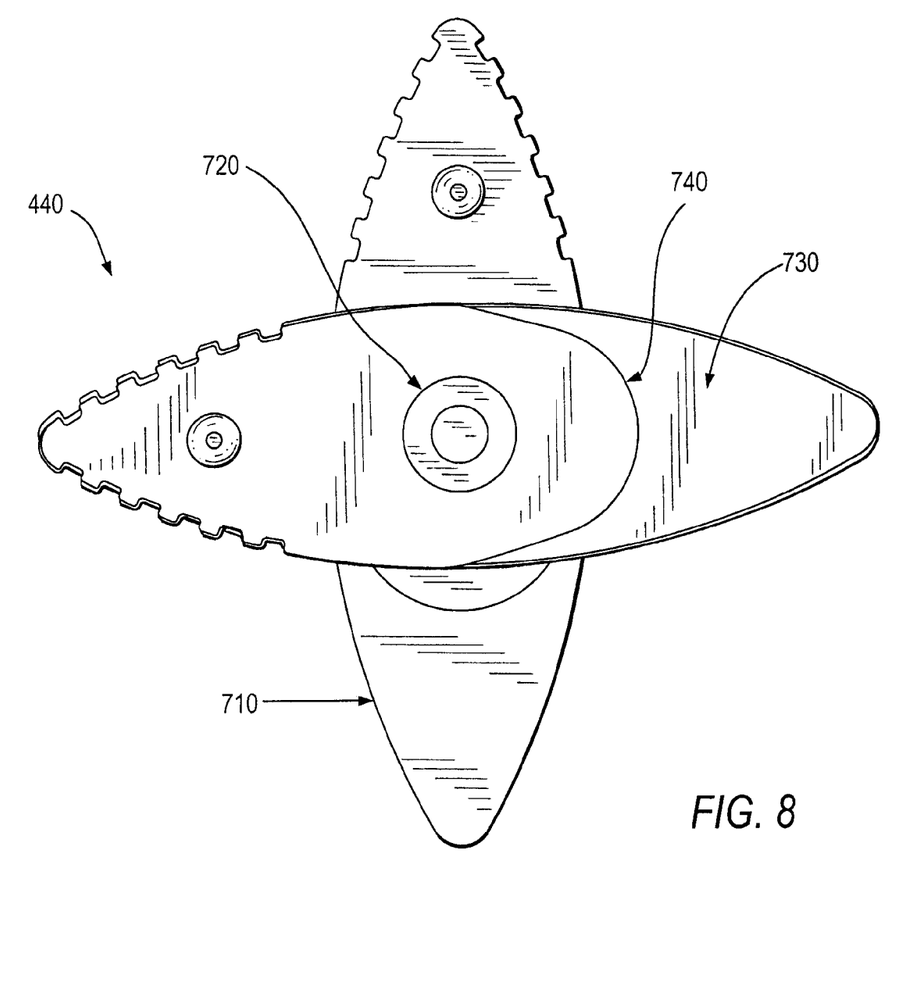
FIG. 8 is a top view of a quick-release support stanchion for mounting a fiberglass board ionization device.

FIG. 7 is a perspective detail of third stanchion 440 which provides board 110 with structural support but does not provide it with any voltage. A plurality of rotating clips 710 rotates around a pivot 720. Another stainless steel threaded rod is used to provide structural support for the third stanchion, though it does not serve a dual function as a power conductor. The top of each rotating clip 710 has a concave notch 730 provides space for board 110. FIG. 8 is a top view of third stanchion 440, and shows that within concave notch 730 is a cam 740. Cam 740 corresponds to the concave notch 260 of board 110. Third stanchion 440 has a minimum of two rotating clips 710, to retain a single board 110, but by varying the number of rotating clips 710, a stanchion can be built to support any of a plurality of boards 110. At the base of the stack of rotating clips 710, the threaded rod penetrates the baseplate on the enclosure. At the top of the stack of rotating clips, washers and nuts are used to retain top rotating clip 710 in place vertically.

With reference to FIG. 4, the lowest board 110 is slid into place with reference to the lowest convex notch 645 of stanchions 420 and 430 and gently pressed into place. The corresponding rotating clip 710 of stanchion 440 is then rotated so that cam 740 will enter into notch 260 of board 110, pushing board forward approximately 0.1" against convex notches 645 of stanchions 420 and 430 to compress board 110 into central conductor 520 and lock board 110 into place. The process is repeated for additional ionization devices 100 desired to be mounted in system 400.

Figure 9:
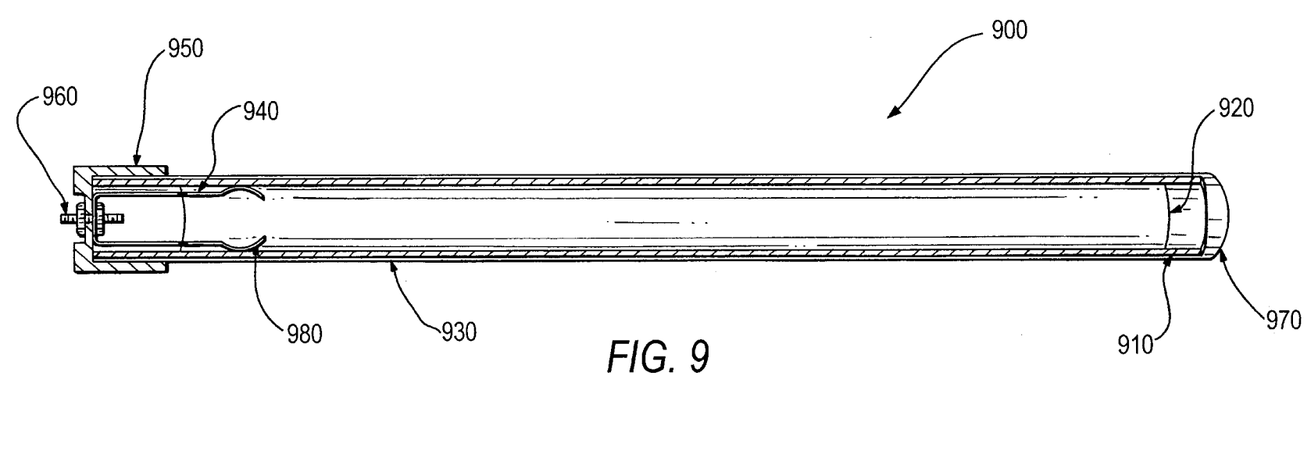
FIG. 9 is a side view of a fiberglass tube ionization device.
Figure 9A:
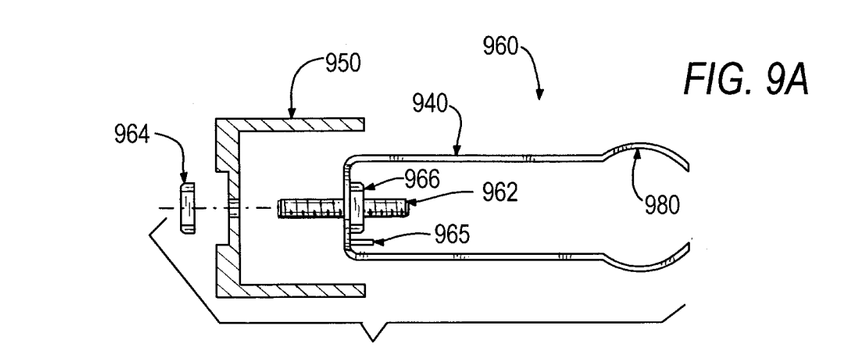
FIG. 9A is a detail showing the assembled conducting terminal and end cap.

FIG. 9 and detail FIG. 9 show yet another embodiment of the present invention, being a bipolar ionization tube 900. The bipolar ionization tube 900 includes a fiberglass tube 910, an end cap 950, a conducting terminal 960, a cathode 920, an anode 930, a seal cap 970, and at least one sealant for securing the end cap 950 and seal cap 970 to the fiberglass tube 910.

The fiberglass tube 910 has an elongated cylindrical shape, with a wall of substantially uniform cross-section, forming an interior surface and an exterior surface. The fiberglass tube 910 has a first end and a second end. In a preferred embodiment, fiberglass tube 910 is preferably rated FR-4 grade. In one embodiment the outer diameter of the fiberglass tube can be approximately 0.75 to 1.625 inches, and is preferably about 1.375 inches. The thickness of the fiberglass wall forming the tube 910 is preferably 0.125 inches to 0.140 inches. In a preferred embodiment, the overall length of the fiberglass tube is 7 inches to 21 inches, although such lengths are not considered limiting. A person of ordinary skill in the art will appreciate that the dimensions of the fiberglass tube 910 are associated with the desired overall ion output and are not considered as limiting. The edge at the first end of the fiberglass tube 910 is seated into the end cap 950, while the edge at the second end of the fiberglass tube 910 is seated into the seal cap 970. End cap 950 and seal cap 970 are formed of an insulating material, such as vinyl.

Arranged against the inner wall of the fiberglass tube 910 is the cathode 920. Preferably, the cathode 920 is formed from solid aluminum alloy and is cylindrical in shape. In a preferred embodiment, the alloy is 1100 H0 series. Although the cathode 920 is described as being fabricated from aluminum, a person of ordinary skill in the art will appreciate that other conductive metals or metal alloys can be utilized to form the cathode 920, such as stainless steel and the like, and in lieu of a solid form, a mesh or perforated form can be used. A thin film of metal can also be created through a version of deposition, such as sputtering, chemical vapor deposition (CVD), etc.

The cathode 920 is sized to cover the interior surface of the fiberglass tube 910, to about ¼"-½" from the edge of the first and second ends of the fiberglass tube 910, allowing enough space at the edges of the fiberglass tube 910 so that the edge of the first end of fiberglass tube 910 may properly fit into the end cap 950 and that the edge of the second end of fiberglass tube 910 may properly fit into seal cap 970. In a preferred embodiment, the cathode 920 has a thickness of approximately 0.010 inches.

The anode 930 is arranged on the outer wall of fiberglass tube 910. The anode 930 is cylindrical in shape and fabricated from a stainless steel mesh, which covers the exterior surface of the fiberglass tube 910. Preferably, the anode 930 is approximately the same or slightly larger that the length of the cathode 920. Although the anode 930 is described as being fabricated from stainless steel, a person of ordinary skill in the art will appreciate that other conductive metals or metal alloys can be utilized to form the cathode 920, such as aluminum and the like.

In a preferred embodiment, the anode 930 has a thickness of approximately 0.14 inches, and 225 openings per square inch. Alternatively, the anode 930 can have a thickness in the range of 0.01 to 0.015 inches, and 180 to 290 openings (i.e., perforations) per square inch.

The anode 930 is electrically connected to a high voltage alternating current power supply with an electrical conductor (not shown), such as a stainless steel clip, wire, or other well-known electrical conductor. In one embodiment, a stainless steel clip extends from the HV+ lead of the high voltage power supply and is positioned to securely contact the outer surface area of the anode 930.

The conducting terminal 960 includes a power input terminal 962, a current distributor 940 with two tines 980, fastener 966 and anti-rotation tab 965 for securing the current distributor 940 to the power input terminal 962, and fastener 964 for securing the assembled conducting terminal 960 to end cap 950.

The power input terminal 962 is made of a conductive metal, such as #304 stainless steel. The power input terminal 962 extends through a bore formed through the floor of the end cap 950. The power input terminal 962 is mechanically and electrically connected to the current distributor 940. In one embodiment, the bottom portion of the current distributor 940 includes a smooth bore sized to receive a threaded end of the power input terminal 962. Fastener 966 for securing current distributor 940 to power input terminal 962 can be a nut, though different methods of fastening may be used, such as welding or screws in various configurations. Likewise, fastener 964 for securing the assembled conducting terminal 960 to end cap 950 can be a nut, though different methods of fastening may be used.

The power input terminal 962 extends a sufficient length from the external surface of the bottom portion of the end cap 950 to allow for connection to the separate high voltage alternating current power supply. The external end of the power input terminal 962 can be a threaded, as illustratively shown, although such terminal connector is not considered as limiting. For example, the power input terminal 962 can be of a plug-in or stab-on type connector, amongst other well-known connectors.

The current distributor 940 is shaped as a U-shaped tuning fork with two tines 980 that extend outward to contact cathode 920. Current distributor 940 is fabricated from a conductive metal, such as stainless steel, aluminum, copper, among other conductive metals or metal alloys.

Similarly to the flat fiberglass board ionization device 100, the bipolar ionization tube 900 can be installed, for example, in a heating, ventilation and cooling (HVAC) duct. During operation, the bipolar ionization tube 900 is connected to a suitable power source, such as a high voltage AC power supply. One polarity is supplied to current distributor 940 and is distributed to the cathode 920 by the current distributor 940 through its tines 980. The opposite polarity is provided to anode 930, such as by a conductive wire or clip provided between the anode and the power source. As described earlier, this leads to opposite charges to build up on each side of the dielectric barrier.

As air flows over the ionization device and the molecules in the air interact with the generated plasma, electrons are transferred between molecules generating both positive and negative ions that propagate quickly; thus ionizing the air. Ionization of the air helps clean the air by breaking down organic chemicals and removing their associated odors, as well as reducing the levels of particulate matter.

It is noted that the design of the anode and cathode, which includes the metals used for fabrication, as well as the increase in the number of perforations per square inch of the stainless steel anode mesh, are specifically directed towards increasing the ionization output in the surrounding air over the prior art. Likewise, the type of dielectric and its thickness, and the spacing between the dielectric and the anode are important in optimizing the ionization output. Advantageously, energy costs to operate the ionization tube 900 of the present invention can be reduced as compared to the tubes of the prior art, since the enhancements to the anode and cathode increase the overall ion production of the tube 900.

Figure 10:
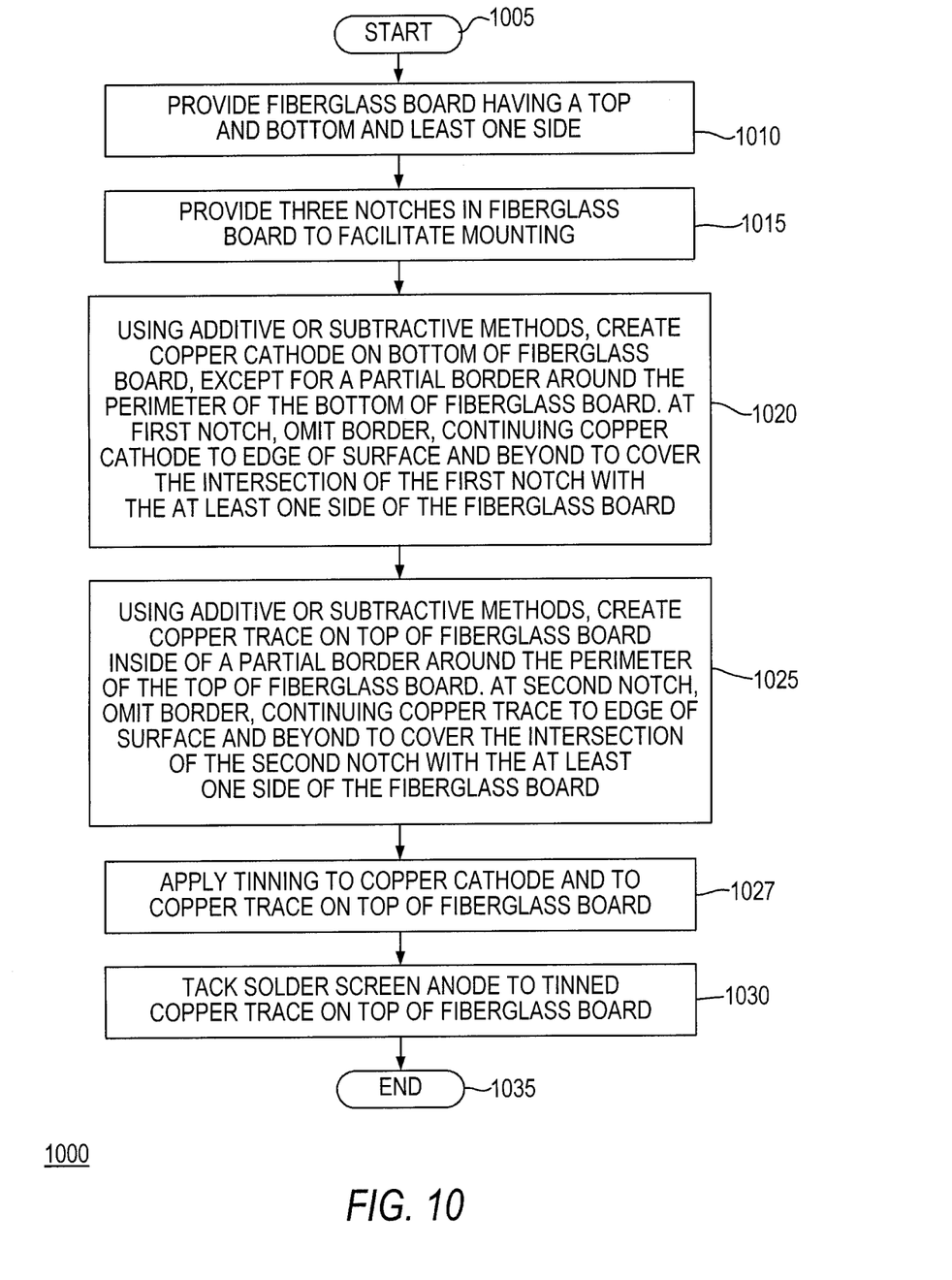
FIG. 10 is a flowchart illustrating a method for fabricating a flat fiberglass ionization device.

Referring to FIG. 10, a method 1000 for fabricating the flat board ionization device 100 of the present invention is illustratively shown in the flow chart. The method 1000 starts at 1005 and proceeds to step 1010, where the fiberglass board 110 is provided, having a top surface, a bottom surface, and at least one side.

At step 1015, fiberglass board 110 is provided with first notch 250, second notch 240, and third notch 260, to facilitate mounting of fiberglass board 110, as well as to provide high voltage alternating current to the anode and cathode via electrical connections at 240 and 250.

At step 1020, either subtractive or additive methods are used to create copper cathode 310 on the bottom of fiberglass board 110, except for a partial border around the perimeter of the bottom of fiberglass board 110. At first notch 250, the border is omitted and the copper continues to the edge of fiberglass board 110 and over the edge, covering part of the intersection of first notch 250 with the side of fiberglass board 110.

In step 1025, either subtractive or additive methods are used to create copper trace 210 on the top of fiberglass board 110 inside of a partial border 220 around the perimeter of the top of fiberglass board 110. At second notch 240, the border 220 is omitted and the copper trace 210 continues to the edge of fiberglass board 110 and over the edge, covering part of the intersection of second notch 240 with the side of fiberglass board 110.

In step 1027, copper cathode 310 is provided with tinning, with heavy tinning where the copper continues over the edge at first notch 250. In addition, copper trace 210 is provided with tinning, with heavy tinning where the copper continues over the edge at second notch 240.

At step 1030, screen 150 is tack soldered to attachment dots 280 and to copper trace 210 at small attachment dots 285, completing construction of anode 115 of the top of fiberglass board 110.

The method 1000 then proceeds to step 1030, where the method ends and any testing of the assembled ionization tube is provided.

Figure 11:
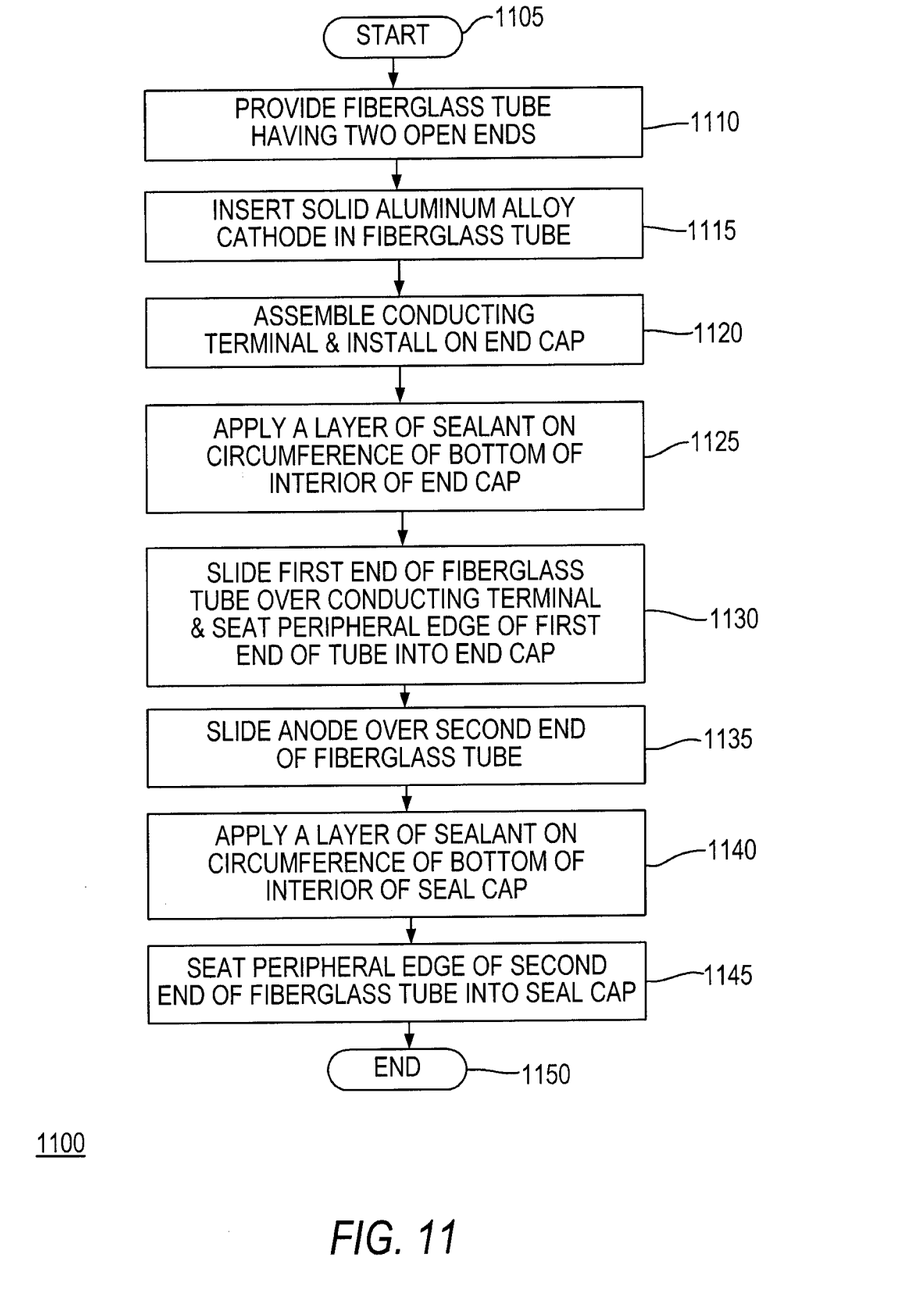
FIG. 11 is a flowchart illustrating a method for fabricating a bipolar ionization tube.

Referring to FIG. 11, a method 1100 for fabricating the bipolar ionization tube 900 of the present invention is illustratively shown in the flow chart. The method 1100 starts at 1105 and proceeds to step 1110, where the fiberglass tube 910 is provided.

At step 1115, solid aluminum alloy cathode 920 is inserted into the interior of the fiberglass tube 910. The cathode 920 is positioned such that the upper and lower edges of the cathode 920 are about ¼"-½" from the edge of the first and second ends of the fiberglass tube 910. As previously discussed for the apparatus, other conductive metals or metal alloys can be utilized to form the cathode 920, such as stainless steel and the like, and in lieu of a solid form, a mesh or perforated form can be used. A thin film of metal can also be created through a version of deposition, such as sputtering, chemical vapor deposition (CVD), etc.

At step 1120, conducting terminal 960 is assembled and installed on end cap 950.

In step 1125, a layer of sealant is applied to the circumference around the bottom of the inside of end cap 950. Depending on the type of sealant, the sealant can be allowed to partially cure prior to proceeding to step 1130.

At step 1130, the first end of fiberglass tube 910 is slid over the conducting terminal 960 and slid downwards towards the end cap 950 until the peripheral edge of the tube 910 is firmly seated at the bottom of the inside of end cap 950. The tines 980 of the current distributor 940 make contact with cathode 920.

At step 1135, the cylindrical stainless steel mesh anode 930 is slid over the second end of the fiberglass tube 910. The upper and lower edges of the anode 930 are aligned to coincide with the respective upper and lower edges of the cathode 920.

In step 1140, a layer of sealant is applied to the circumference around the bottom of the inside of seal cap 970. Depending on the type of sealant, the sealant can be allowed to partially cure prior to proceeding to step 1145.

At step 1145 the peripheral edge of the second end of fiberglass tube 910 is firmly seated at the bottom of the inside of seal cap 970.

The method 1100 then proceeds to step 1150, where the method ends and any additional curing of the sealants and testing of the assembled ionization tube is provided.

A person of ordinary skill in the art will appreciate that the specific order of the steps of method 1100 is not considered limiting.

Although an exemplary description of the invention has been set forth above to enable those of ordinary skill in the art to make and use the invention, that description should not be construed to limit the invention, and various modifications and variations may be made to the description without departing from the scope of the invention, as will be understood by those with ordinary skill in the art, and the scope thereof is determined by the claims that follow.

The invention claimed is:

1. A bipolar ionization tube, comprising:
    a fiberglass tube with a first end and a second end;
    a cathode positioned within and being circumscribed by an interior surface wall of said fiberglass tube;
    an anode circumscribing an exterior surface of said fiberglass tube, said anode configured for electrical connectivity with a first conducting terminal of a power supply;
    an electrically insulated end cap sized for receiving the first end of said fiberglass tube, said end cap being secured to said fiberglass tube with at least one sealant;
    an elongated conducting terminal having a first portion extending through said end cap and configured for electrical connectivity with a second conducting terminal of said power supply, and a second portion extending into said fiberglass tube and configured for electrical connectivity with said cathode; and
    a seal cap sized for receiving the second end of said fiberglass tube, said seal cap being secured to said fiberglass tube with the at least one sealant.

2. The bipolar ionization tube of claim 1, wherein said cathode is cylindrically shaped and fabricated from solid aluminum alloy.

3. The bipolar ionization tube of claim 1, wherein said anode is cylindrically shaped and fabricated from a stainless steel mesh.

4. The bipolar ionization tube of claim 3, wherein the second portion of said elongated conducting terminal comprises a conductive current distributor member for providing current to said cathode.

5. The bipolar ionization tube of claim 4, wherein said conductive current distributor member includes a plurality of tines for contacting said cathode.

* * * * *